US007407816B2

(12) United States Patent
Kozulic

(10) Patent No.: US 7,407,816 B2
(45) Date of Patent: Aug. 5, 2008

(54) ISOELECTRIC PARTICLES AND USES THEREOF

(75) Inventor: Branko Kozulic, Zurich (CH)

(73) Assignee: Gentius, Inc, Zadar (HR)

( * ) Notice: Subject to any disclaimer, the term of this patent is extended or adjusted under 35 U.S.C. 154(b) by 437 days.

(21) Appl. No.: 10/840,347

(22) Filed: May 7, 2004

(65) Prior Publication Data
US 2005/0250220 A1 Nov. 10, 2005

(51) Int. Cl.
G01N 33/551 (2006.01)
(52) U.S. Cl. .................................. 436/524; 436/528
(58) Field of Classification Search ......... 436/514–518, 436/523–535, 546; 435/4, 7.92
See application file for complete search history.

(56) References Cited

U.S. PATENT DOCUMENTS

| | | | |
|---|---|---|---|
| 3,485,736 A | | 12/1969 | Vesterberg |
| 3,925,152 A * | | 12/1975 | Porath et al. ................. 435/239 |
| 4,130,470 A | | 12/1978 | Rosengren |
| 4,131,534 A | | 12/1978 | Just |
| 4,139,440 A | | 2/1979 | Chreambach et al. |
| 4,139,499 A * | | 2/1979 | Wade et al. .................... 521/32 |
| 4,326,008 A | | 4/1982 | Rembaum |
| 4,334,972 A | | 6/1982 | Soderberg |
| 4,415,665 A | | 11/1983 | Mosbach et al. |
| 4,521,317 A | | 6/1985 | Candau et al. |
| 4,552,839 A * | | 11/1985 | Gould et al. .................... 455/7 |
| 4,560,714 A | | 12/1985 | Gajiria et al. |
| 4,609,608 A | | 9/1986 | Solc |
| 4,609,689 A | | 9/1986 | Schwartz et al. |
| 4,680,201 A | | 7/1987 | Hjerten |
| 4,681,912 A | | 7/1987 | Durand |
| 4,725,343 A | | 2/1988 | Hjerten |
| 4,749,506 A | | 6/1988 | Kitahara et al. |
| 4,788,246 A | | 11/1988 | Tsuchiya et al. |
| 4,931,328 A | | 6/1990 | Swedberg |
| 4,954,399 A * | | 9/1990 | Tani et al. ................. 428/402 |
| 4,971,670 A | | 11/1990 | Faupel et al. |
| 5,069,766 A | | 12/1991 | Zhu et al. |
| 5,084,150 A | | 1/1992 | Karger et al. |
| 5,091,206 A | | 2/1992 | Wang et al. |
| 5,110,434 A | | 5/1992 | Zhu et al. |
| 5,137,609 A | | 8/1992 | Manian et al. |
| 5,171,808 A | | 12/1992 | Ryles |
| 5,202,007 A | | 4/1993 | Kozulic |
| 5,221,447 A | | 6/1993 | Hjerten |
| 5,286,803 A | | 2/1994 | Lindsay et al. |
| 5,319,046 A | | 6/1994 | Kozulic |
| 5,348,633 A | | 9/1994 | Karger et al. |
| 5,354,481 A | | 10/1994 | Neff et al. |
| 5,376,249 A | | 12/1994 | Afeyan et al. |
| 5,380,444 A | | 1/1995 | Ryan et al. |
| 5,412,048 A | | 5/1995 | Longley et al. |
| 5,447,612 A | | 9/1995 | Bier et al. |
| 5,468,359 A | | 11/1995 | Pawliszyn |
| 5,536,382 A | | 7/1996 | Sunzeri |
| 5,573,909 A | | 11/1996 | Singer et al. |
| 5,605,613 A | | 2/1997 | Shieh |
| 5,607,864 A | | 3/1997 | Ricciero et al. |
| 5,630,924 A | | 5/1997 | Fuchs et al. |
| 5,635,574 A | | 6/1997 | Aoyagi |
| 5,641,634 A | | 6/1997 | Mandecki |
| 5,716,855 A | | 2/1998 | Lerner et al. |
| 5,786,219 A | | 7/1998 | Zhanh et al. |
| 5,810,985 A | | 9/1998 | Bao et al. |
| 5,824,478 A | | 10/1998 | Muller |
| 5,866,683 A | | 2/1999 | Shimura et al. |
| 5,897,811 A | | 4/1999 | Lesko |
| 5,958,202 A | | 9/1999 | Regnier et al. |
| 5,976,426 A | | 11/1999 | Richard |
| 6,013,531 A | | 1/2000 | Wang et al. |
| 6,133,047 A | | 10/2000 | Elaissari et al. |
| 6,136,891 A | | 10/2000 | Chopin et al. |
| 6,197,906 B1 | | 3/2001 | Soloman et al. |
| 6,214,560 B1 | | 4/2001 | Yguerabide |
| 6,235,483 B1 * | | 5/2001 | Wolber et al. ................. 435/6 |
| 6,251,303 B1 | | 6/2001 | Bawendi et al. |
| 6,274,387 B1 | | 8/2001 | Yamauchi et al. |
| 6,355,431 B1 | | 3/2002 | Chee et al. |
| 6,372,428 B1 | | 4/2002 | Nova et al. |
| 6,465,193 B2 | | 10/2002 | Akeson et al. |
| 6,514,295 B1 | | 2/2003 | Chandler et al. |
| 6,541,039 B1 | | 4/2003 | Lesniak et al. |
| 6,548,264 B1 | | 4/2003 | Tan et al. |
| 6,585,873 B1 | | 7/2003 | Solomon et al. |
| 6,590,051 B1 | | 7/2003 | Carter et al. |
| 6,638,408 B1 | | 10/2003 | Speicher et al. |
| 6,642,318 B1 | | 11/2003 | Chiefari et al. |
| 6,642,351 B1 * | | 11/2003 | Harlukowicz et al. ... 528/502 R |
| 6,654,505 B2 | | 11/2003 | Bridgham et al. |
| 6,673,550 B2 | | 1/2004 | Matray et al. |

(Continued)

FOREIGN PATENT DOCUMENTS

EP  0 335 703  10/1989

(Continued)

OTHER PUBLICATIONS

Abramson et al., "Electrokinetic Phenomena. XIII. A Comparison of the Isoelectric Points of Dissolved and Crystalline Amino Acids", The Journal of General Physiology, (1938), pp. 729-744.*

(Continued)

Primary Examiner—Ann Y Lam
(74) Attorney, Agent, or Firm—Michael G. Gilman

(57) ABSTRACT

A plurality of particles of from about 5 nm to 100 μm possessing predetermined isoelectric points in the pH range from about 2.5 to 11 is used in a method of detection of a plurality of analytes, wherein the isoelectric particles of each isoelectric point further contain a label and a member of a binding pair capable of interacting with a selected analyte. The particles that formed specific binding pairs are recovered and separated by isoelectric focusing, followed by the detection of the labels associated with the particles. A flow cytometer may be used as a detector of the isoelectric particles.

13 Claims, No Drawings

U.S. PATENT DOCUMENTS

| | | | |
|---|---|---|---|
| 6,682,887 | B1 | 1/2004 | Singh et al. |
| 6,686,152 | B2 | 2/2004 | Singh et al. |
| 6,696,304 | B1 | 2/2004 | Davies |
| 7,169,275 | B2 * | 1/2007 | Eckerskorn et al. ......... 204/450 |

FOREIGN PATENT DOCUMENTS

| WO | WO 03/101494 | 12/2003 |
|---|---|---|

OTHER PUBLICATIONS

Baade et al. Kinetics of the dispersion polymerization of acrylamide, *European Polymer Journal* 20:505-512 (1984).

Bellini et al. Synthesis of zwitterionic acrylic acid buffers for isoelectric focusing in immobilized pH gradients, *Electrophoresis* 19:1590-1595 (1998).

Chen et al. Dynamic enhancements of sample loading and analyte concentration in capillary isoelectric focusing for proteome studies, *Journal of Proteome Research* 2:249-254 (2003).

Chiari et al. Physico-chemical properties of amphoteric, isoelectric, macroreticulate buffers, *Journal of Biochemical and Biophysical Methods* 23:115-130 (1991).

Chiefari et al. Living free-radical polymerization by reversible addition-fragmentation chain transfer: The RAFT process, *Macromolecules* 31:5559-5562 (1998).

Cretich et al. Separation of proteins in a multicompartment electrolyzer with chambers defined by a bed of gel beads, *Electrophoresis* 24:577-581 (2003).

Cruickshank et al. Simultaneous multiple analyte detection using fluorescent peptides and capillary isoelectric focusing, *Journal of Chromatography A* 817:41-47 (1998).

Hofmann et al. Adaptation of capillary isoelectric focusing to microchannels on a glass chip, *Analytical Chemistry* 71:678-686 (1999).

Kawaguchi et al. Hydrogel microspheres II. Precipitation copolymerization of acrylamide with comonomers to prepare monodisperse hydrogel microspheres, *Polymer Journal* 23: 955-962 (1991).

Kim et al. Preparation and characterization of monodisperse polyacrylamide microgels, *Polymer Journal* 27:508-514 (1995).

Lowe et al. The preparation and physico-chemical properties of poly(N-ethylacrylamide) microgels, *Polymer* 5:1207-1212 (1998).

Luxton et al. Use of external magnetic fields to reduce reaction times in an immunoassay using micrometer-sized paramagnetic particles as labels (magnetoimmunoassay) *Analytical Chemistry* 76:1715-1719 (2004).

Murray et al. The preparation, characterization and applications of colloidal microgels, *Advances in Colloid Interface Science* 54:73-91 (1995).

Righetti, P.G. in *Immobilized pH Gradients: Theory and Methodology*, Elsevier, Amsterdam, 1990.

Zwitterionic Latex Particles as an Effective Carrier for DNA T. Somasundaran et al.; Journal of Colloid and Interface Science 246, 223-226 (2002).

Colloidal Propperties and Protein Adsorption of Amphoteric Microspheres Shi-Jiang Fang et al.;Colloids and Surfaces A: Physiochem. Eng. Aspects 211, 79-84 (2001).

A Thermosensitive Amphoteric Microsphere and its Potential Application as a Biological Carrier Shi-Jiang Fang et al.; Colloid Polym Sci. 280, 984-989 (2002).

Electrostatic Interactions Between Amphoteric Latex Particles and Proteins Chorng-Shyan Chern et al. Colloid Polym Sci. 283, 257-264 (2004).

Synthesis and Characterization of Amphoteric Latex Partcles Chorng-Shyan Chern et al. Colloid Polym Sci. 281, 1092-1089 (2003).

* cited by examiner

ISOELECTRIC PARTICLES AND USES THEREOF

BACKGROUND OF THE INVENTION

1. Field of the Invention

The field of this invention relates to novel particles useful for detecting a plurality of specific binding interactions, especially the interactions in which at least one member is a biological molecule.

2. Background

Sensitive and specific methods are needed for quantitative analysis of trace amounts ($10^{-8}$-$10^{-10}$ M) of analytes in a sample. Direct measurements are usually difficult or impossible, because either the analyte does not possess a physical or chemical property (e.g., fluorescence) that is easily measurable, or because the sample contains interfering substances. A common approach to overcome this difficulty relies on the formation of a specific binding pair between an analyte of interest and a second member of a binding pair, with an easily detectable label linked to the second member of the binding pair. Specific binding pairs most commonly employed comprise antibody-antigen or antibody-hapten, ligand-receptor, lectin-sugar, avidin-biotin, DNA-DNA, DNA-RNA and RNA-RNA, where the nucleic acids may be of natural or synthetic origin.

There exist many assay formats that take advantage of a high specificity of the formation of properly selected binding pairs, including ELISA, RIA, immunoblotting, immunochromatographic, Southern blotting, Northern blotting, affinity chromatography and affinity electrophoresis. Such assays are usually carried out with the aim of detecting the presence and concentration of just one analyte or a small number of analytes. High throughput methods that rely on the formation of many binding pairs of one type such as DNA-DNA, having the capability of simultaneously detect hundreds, or thousands, of analytes are also known. Thus, DNA microarrays may contain tens of thousands of short oligonucleotides that are immobilized on a solid surface and are able to hybridize with tens of thousands of DNA fragments of complementary sequences suspected to be present in a sample. Current antibody arrays are suitable for the analysis of hundreds of antigens in a sample. While the DNA and protein microarrays have greatly increased our ability to analyze multiple analytes in biological samples, one of their drawbacks is the inherent difficulty to perform quality control of the individual microarrays. Other high throughput methods exist as well. Thus, an alternative to an array of spots characteristic for DNA and protein microarrays is an array of beads (U.S. Pat. No. 6,654,505 to Bridgham et al. and U.S. Pat. No. 6,355,431 to Chee et al.). A fiber optics device can be used with a bead array instead of a scanner or a CCD device usually employed for detecting the formation of specific binding pairs of DNA and protein micrarrays. Another method relies on the formation of specific binding pairs in a solution on the surface, of dispersed beads that are coded with various fluorescent dye combinations, so that each bead can be identified on the basis of its unique dye composition (U.S. Pat. No. 6,514,295 to Chandler et al.). Analytes are detected and quantified based on the fluorescence emitted by another dye linked to a second member that has participated in the formation of a specific binding pair at the surface of the color coded beads.

3. Description of Related Art

Electrophoretic methods have also been employed for detecting the formation of specific binding pairs. Thus, U.S. Pat. No. 5,084,150 to Karger et al. discloses a method combining electrophoresis and chromatography wherein charged colloidal particles selectively interact with analytes through affinity groups attached to the surface of the particles. The analytes distribute themselves between the electrophoresis medium and particles, so that migration rates of the analytes are determined by the equilibrium constants and the migration rate of the colloidal particles. U.S. Pat. No. 5,137,609 to Manian et al. discloses a differential separation assay wherein an analyte is reacted with excess of a fluorescently labeled second member of a binding pair, followed by the detection of the free and bound second member using pre-calibrated migration times of the two species.

U.S. Pat. No. 5,536,382 to Sunzeri discloses a capillary electrophoresis method for detecting an analyte is a clinical sample, based on electrophoretic separation of the unbound from bound analyte followed by their detection. Bao et al. in U.S. Pat. No. 5,810,985 disclose an electrochemically mediated chemical analysis wherein an analyte is introduced into a capillary containing a reagent whose contact with the analyte results in forming, or breaking, of a covalent bond. As either the analyte or the reagent is charged, the formation or breaking of a covalent bond causes a change in electrophoretic mobility of the analyte. U.S. Pat. No. 5,958,202 to Regnier et al. discloses a capillary electrophoresis enzyme immunoassay wherein a competitor mediates either the formation or depletion of a detectable product in a capillary subjected to an electric potential. In U.S. Pat. No. 5,630,924 Fuchs et al. disclose a method for analyte detection based on the formation of a three-member complex, including a first binding member carrying a detectable label, the analyte, and a second binding member comprising a charge-modifying moiety. During electrophoresis, the three-member complex is separated from the free first member that carries the label. In U.S. Pat. No. 6,673,550 Matray et al. disclose electrophoretic tag (e-tag) reagents comprising fluorescent compounds and mobility modifiers, wherein after the formation of specific binding pairs the tags are released by cleaving a cleavable linkage by oxidation. The mobility modifier has from 1 to 200 atoms and after the release of the specific biding member the remaining detectable group and the mobility modifier combined have a molecular weight of about 150 to 10,000 Daltons. A large number of specific label-mobility modifier pairs, each with a defined charge/mass ratio and therefore electrophoretic mobility, can be combined with various specific binding members to tag a large number of analytes (commercialized by Aclara, Mountain View, Calif.). U.S. Pat. No. 6,682,887 to Singh et al. discloses the use of electrophoretic tags for the analysis of specific nucleic acid sequences, wherein the detection sequence forming a specific binding pair is degraded to release the e-tag. In U.S. Pat. No. 6,686,152 Singh et al. disclose a method employing e-tags for detecting multiple nucleic acid sequences, wherein a nuclease cleavage releases the e-tags that are subsequently detected based on their unique electrophoretic mobility.

Another electrophoretic method, isoelectric focusing (IEF), has also been used for the detection of analytes. In isoelectric focusing, under the influence of an electric field, a molecule migrates in a medium of a defined pH gradient till it reaches a point where it carries no net charge, that is, till it reaches its isoelectric point (pI). At that point the pH of the medium is identical to the pI of the molecule. Isoelectric focusing is an equilibrium method, in contrast to electrophoresis performed in a medium without a pH gradient. In U.S. Pat. No. 5,348,633 Karger et al. disclose a capillary isoelectric focusing method for detecting analytes by the use of antibody Fab' fragments labeled with a fluorescent dye, wherein the specific binding pairs and free antibody fragments are separated and detected. U.S. Pat. No. 5,376,249 to Afeyan et al. discloses a method of analysis utilizing isoelectric focusing wherein a detector is positioned at a predetermined spot along the capillary length corresponding to the isoelectric point of a binding pair formed between the analyte and an analyte-specific binding moiety.

In U.S. Pat. No. 5,824,478 Müller discloses a diagnostic method and probes wherein an analyte is contacted with a detector probe and a capture probe, with the detector probe including a moiety having a predetermined pI and a detectable label. Specificity of this method relies on the formation of a binding pair between the capture probe and the analyte. The analyte participates also in formation of another binding pair, with a detector probe. The moiety that defines a pI is released from the binding pair prior to its detection by isoelectric focusing. In a detector probe consisting of phycoerythrin-streptavidin, streptavidin served as a group specific (not analyte specific) binding member capable of interacting with all molecules containing a biotin group, while the highly fluorescent protein phycoerythrin was both the label and the pI determining moiety. As disclosed further in U.S. Pat. No. 5,824,478, a chemical treatment of phycoerythrin, or phycoerythrin-avidin complex, may result in production of modified proteins that have pI values in the pH range of 6-9. However, attempts to fractionate these modified proteins into useful fractions of defined pI values proved to be difficult, as subsequently described by Cruickshank et al. in Journal of Chromatography A 817:41-47, 1998. Instead, small synthetic peptides, from three to eight residues, labeled with a fluorescent dye were found to provide the required moieties of defined isoelectric points. The fluorescently labeled peptides had to be released from specific binding pairs prior to isoelectric focusing. While the use of small peptides represents an improvement, the method disclosed by Müller et al. and further described by Cruickshank et al. still suffers from drawbacks. Thus, the need for two probes, a detector probe and an analyte-specific capture probe, makes the method complex and expensive. The need to release the moiety that contains a label and determines the pI prior to isoelectric focusing increases complexity of the method and may result in undesirable side reactions, some of which were described in the Journal of Chromatography article. In addition, many biological samples contain proteases that could degrade the peptides serving as the analyte specific tags. Such protease degradation could lead to misinterpretation of results, because the signal from a degraded tag would be absent, or the signal would be lower in the case of partial degradation of the tag, or a degraded tag could be mistaken for another tag in the case that the degraded tag is of a similar or identical pI as one of the original tags. Finally, this method suffers from a low sensitivity of analyte detection, because it relies on the attachment of a single dye molecule to the peptide moiety having a defined pI. In U.S. Pat. No. 5,824,478 Müller mentioned a possibility of using a moiety having many fluorescent molecules, specifically, a dextran microparticle of several nanometers diameter, produced by Molecular Probes, Eugene, Oreg., wherein the microparticle would be linked to a detector probe by a polystyrene spacer-arm containing a cleavable bridge, such as a disulfide bond. It was not disclosed, however, how such a fluorescent dextran particle could become a moiety with a defined isoelectric point, the requirement necessary for functioning of the method of U.S. Pat. No. 5,824, 478.

From the above description it is evident that there still exists a need for a method that could realize all the benefits of employing isoelectric focusing for analyte detection. Such a method, based on a novel isoelectric particle, is disclosed herein.

SUMMARY OF THE INVENTION

A synthetic, non-peptide particle having isoelectric point (pI) of a predetermined value and capable of focusing in a pH gradient under the influence of an electric field is used as a tag or a coding composition. A plurality of such particles having different isoelectric points and containing a label is used to tag a plurality of different binding members. Differences in isoelectric points between various particles are such that upon isoelectric focusing the particles of defined isoelectric points form separate zones that are detectable using a suitable detector. A label having defined properties may be attached to a set of particles having different pI. When the detector is capable of detecting multiple labels, then groups of particles of one specific pI may be labeled with different labels, each combination of a label-isoelectric particle-binding member being related to a specific analyte.

A method of analyte detection uses a labeled isoelectric particle with a bound first member of a binding pair, wherein the first member of the binding pair is capable of interacting with the analyte or an analyte analogue. The particles that have participated in the formation of specific binding pairs are isolated and detected by the method of isoelectric focusing. The isoelectric particles of one predetermined pI may be labeled with different labels in order to increase the capability of detection of multiple analytes in a sample. If 140 groups of particles of different pI values are labeled each with 100 different dyes, it is possible to analyze 14,000 analytes in a sample. In another method, combinations of the isoelectric particles and dyes, without a binding member, are used for tracing materials whose traceability is desirable.

A kit is provided comprising the isoelectric particles and other components and reagents necessary for performing an analysis using the method of present invention.

Thus, this invention contemplates particles of a size from about 5 nm to 50 μm and of a predetermined isoelectric point in the pH range from about 2.5 to 11 containing at least 100 positively and negatively charged groups comprising at least one organic acid and at least one organic base linked by non-peptide bonds, wherein the charged groups define the isoelectric point of the particle and wherein, when subjected to an electric field, the particle is capable of migrating in a medium containing a pH gradient and to focus at a position in the pH gradient that corresponds to its isoelectric point.

DESCRIPTION OF THE SPECIFIC EMBODIMENTS

In accordance with the present invention, novel materials and methods are provided for rapid, sensitive and accurate detection of a plurality of analytes in a sample or of a single analyte in many samples. Novel materials are the particles with a predetermined isoelectric point capable of migrating in an electric field and focusing at their isoelectric points. The methods comprise using as reagents a mixture of such isoelectric particles together with members of binding pairs and labels. Each combination of the particles of a predetermined isoelectric point, a label and a first binding member represents a unique coding composition for detecting a second binding member, that is, the analyte. The coding composition relies on the properties of the particle, and it cannot be determined free of the particle.

Isoelectric point, or pI, corresponds to a pH value at which a molecule or a particle is electrically neutral. At that pH value, the particle does not migrate in an electric field. The isoelectric particle of present invention may comprise organic material or a combination of organic and inorganic material.

Suitable organic materials include synthetic and natural polymers, while examples of suitable inorganic materials include glass, silica, gold and CdS. When a combination of an organic and inorganic material is used according to the present invention, then the isoelectric point of the particle is determined by its organic component.

The particles are generally of spherical shape, but irregular shapes are suitable as well. The size of the particles is in the range of about 5 nm to 100 µm, more usually in the range of about 30 nm to 50 µm. Size of the particles plays a role only as much as it influences the ability of the particles to migrate and focus at their isoelectric point using a selected isoelectric focusing method. In a set of particles having different pI values, all particles in the set may be substantially of equal size. Or, particles of different pI values may have different sizes. Also the particles of a defined pI value may have different sizes. However, it is preferable that size differences are small among the particles of a defined pI. Density of the particles may vary from about 0.7 to 1.5 g/ml, or more. A preferable density is the one similar to the density of the medium used for isoelectric focusing of the particles.

The isoelectric particles of present invention carry a label. The label may be present in a precursor particle before an isoelectric particle is produced, or it can be incorporated simultaneously with the production of the particle, or it can be attached to the particle after its production. The label remains bound to the particle throughout the whole analysis.

In a method of analyte detection, the isoelectric particles also carry at least one member of at least one binding pair. The member is linked to the particle through at least one covalent bond or non-covalent bond. Covalent bonds are preferred. The member of the specific binding pair may remain bound to the particle throughout the whole analysis, or it may be released from the particle prior to the isoelectric focusing step.

Isoelectric point of the particles of present invention is determined by charged groups that the particle contains. Each particle has both positive and negative charges. Positive charges come mainly from protonated bases whereas negative charges come mainly from deprotonated acids. The ratio of the positive and negative charges and the pK values of the acidic and basic groups determine the isoelectric point. The particles will have isoelectric point in the pH range of about 2 to 11.5, more commonly in the pH range of about 2.5 to 11 and most commonly from about 3 to 10. The particles of a low isoelectric point have a high proportion of acidic (negatively charged) groups of low pK values, while the particles of a high isoelectric point have a high proportion of basic (positively charged) groups of high pK values. Suitable acidic groups include, for example, carboxylic acids, phosphoric acids, phosphonic acids and sulfonic acids, while basic groups may be amino and guanidino groups. Amino groups can be primary, secondary or tertiary. Quaternary ammonium groups may be included as well.

Various kinds of labels may be used in combination with the isoelectric particles of present invention. They include, for example, fluorescent compounds, dyes, light scattering particles, magnetic compounds and radioactive compounds. The only limitations imposed on the nature of the label are that it must be sufficiently small, that it should not interfere with the isoelectric focusing and that it should be detectable during or after the isoelectric focusing step. A corresponding detector will be used for measuring a signal characteristic for each kind of the label, including fluorescence, absorbance, light scattering, magnetic filed or radioactivity, respectively. Other labels and detectors will be known to those skilled in the art. A combination of different kinds of labels, and corresponding detectors, may be employed.

To be useful for detecting a specific analyte, the isoelectric particle of the present invention carries a binding member which is capable of forming a specific binding pair with the analyte. A specific binding pair is defined as a pair of molecules that have affinity for each other characterized by an association constant of at least $10^5$ l mol$^{-1}$. The binding member may be bound or attached only to the surface of the particle, or it may also reside in interior of the particle. A short spacer, or a long one, may serve as a bridge between the binding member and the particle surface. When a long polymeric spacer is used, then more than one binding member may be linked to a single spacer. The spacer serves to facilitate the interaction between the members of the binding pair by reducing the steric hindrance. The specific binding pairs comprise antibodies and antigens or haptens, receptors and ligands, lectins and polysaccharides, enzymes and inhibitors, hybridizable nucleic acids, and the like.

To be useful for analyte detection, the isoelectric particles of present invention need to be brought to their isoelectric points using the method of isoelectric focusing. One method of isoelectric focusing relies on compounds, known as ampholytes, having several carboxylic and amino groups and possessing a buffering capacity at their isoelectric point. Their synthesis is disclosed in U.S. Pat. No. 3,485,736 to Vesterberg, U.S. Pat. No. 4,131,534 to Just and U.S. Pat. No. 4,334,972 to Söderberg. When a mixture of ampholytes, in a gel or in a tube, is subjected to an electric field where the anode is in contact with an acidic solution and the cathode with a basic solution, each individual ampholyte molecule migrates till it reaches its isoelectric point, and a train of the ampholyte molecules establishes a pH gradient in the gel or in the tube. When other amphoteric molecules, that is, the molecules possessing an isoelectric point, such as proteins or peptides, are present in the gel or tube, they also focus at their isoelectric point. Thus, a mixture of proteins or peptides is separated based on the differences in their isoelectric points. Synthetic ampholytes, known also as carrier ampholytes, are commercially available from many vendors under different trade names, including Ampholines and Pharmalytes (Amersham Pharmacia Biotech, Uppsala, Sweden), Biolytes (Bio-Rad, Hercules, Calif.) and Servalytes (Serva, Heidelberg, Germany). Another method of isoelectric focusing relies on a pH gradient created by vinyl monomers containing charged groups, as disclosed in U.S. Pat. No. 4,130,470 to Rosengren et al., or described by Bellini et al. (Electrophoresis 19:1590-1595, 1998). The pH gradient is formed by mixing at least two solutions of gel forming monomers, of which one contains at least one monomer with a basic group while the other contains at least one monomer with an acidic group at selected concentrations, followed by gel polymerization. The formed gel, which is usually in the form of a sheet, contains acidic and basic groups whose relative ratio varies along the gel length. In effect, casting this gradient gel is equivalent to titrating a base with an acid (or vice versa), followed by immobilization of both the basic and acidic groups in the three dimensional polymer network. Thus, this pH gradient, known under the name immobilized pH gradient (IPG), exists independent of an electric field, in contrast to the pH gradient created by carrier ampholytes. Many immobilized pH gradient gels are commercially available, for example from Amersham, Bio-Rad and Invitrogen (Carlsbad, Calif.). Available from Fluka (Buchs, Switzerland), under the trade name acrylamido buffers, are also 13 individual monomers with basic or acidic groups having pK values from about 1 to about 12. Isoelectric focusing has become a standard method for protein separation and those skilled in the art know how to use it. Most vendors provide detailed instructions that can be of help to those not skilled in the art, and additional details can be found in scientific literature, some of which is cited below.

Several different procedures may be used to incorporate selected charged groups, in a selected ratio to achieve the desired pI value, in order to produce isoelectric particles of the present invention. According to one embodiment, when the desired acidic groups are carboxylic groups and the desired basic groups are amino groups, a mixture of carrier ampholytes is fractionated into fractions having a narrow pH distribution, for example less than about 0.1 pH units. This may be achieved by focusing carrier ampholytes in an immobilized pH gradient gel, followed by cutting the gel into narrow strips and recovering the ampholytes from individual strips. The recovery may be accomplished simply by allowing the ampholytes to diffuse out of the gel. If this procedure is repeated over the pH range spanning 8 units, between pH 3.0 to 11.0, then 80 such fractions will be recovered. Next, each narrow pH ampholyte fraction is incubated with particles having reactive groups capable of forming covalent bonds with ampholyte molecules. One kind of such a reactive group is epoxide, which will react with a primary or secondary amino group of the ampholyte. Another reactive group is aldehyde, which in the presence of a reducing agent, such as sodium cyanoborohydride or sodium borohydride, reacts with amino groups of the ampholyte to form stable bonds. Yet another reactive group is aryl- or alkylsulfonyl, for example 2,2,2-trifluoroethanesulfonyl group (U.S. Pat. No. 4,415,665 to Mosbach et al.). In this way, 80 different isoelectric particles of a predetermined pI may be produced. However, this procedure is a less preferred one.

According to another embodiment, a solution is prepared containing at least one selected basic monomer and at least one selected acidic monomer whose molar ratio is selected such that the solution has a desired pH value. As mentioned above, such charged acrylamide monomers are available from Fluka, and they have the following pK values: 1, 3.1, 3.6, 4.6, 6.2, 6.6, 6.85, 7.0, 7.4, 8.5, 9.3, 10.3 and >12. The first and the last monomer, with the pK value of 1 (the monomer contains a sulfonic acid group) and with the pK above 12 (quaternary ammonium group), are used only as titrants, that is, non-buffering monomers, whereas all other monomers are the buffering monomers. Any desired pH value can be calculated using the Henderson-Hasselbach equation for an acidic monomer titrated with a basic monomer whose pK is about 3 pH units higher than the pK of the acidic monomer:

$$pH = pK_A + \log[C_B/(C_A - C_B)] \quad \text{Equation 1}$$

where $pK_A$ is the pK value of an acidic buffering monomer, while $C_A$ and $C_B$ are the molar concentrations of the acidic and basic monomer, respectively. When a basic monomer is titrated with an acidic monomer, the pH value can be calculated from a similar equation:

$$pH = pK_B + \log[(C_B - C_A)/C_A] \quad \text{Equation 2}$$

where $pK_B$ is the pK value of a basic buffering monomer.

For example, mixing 0.753 ml of a monomer with pK4.6 and 0.137 ml of the monomer with pK9.3, where solutions of both monomers are 0.2M, and the final volume is 15 ml, gives a pH value of 4.03±0.03 (at 20° C.). This example is taken from a book *Immobilized pH Gradients: Theory and Methodology* (by P. G. Righetti, Elsevier, Amsterdam, 1990), which describes also the formulations where more than one acidic or more than one basic monomer is used (pages 64-67). For example, the pH value of 5.69±0.04 (at 20° C.) is obtained by mixing 0.863 ml of the monomer with pK4.6, 0.863 ml of the monomer with pK8.2 and 0.103 ml of the monomer with pK9.3, where all monomer solutions are 0.2M and the final volume is 15 ml. Over 50 different formulations are tabulated in the specified book (pages 64-67). Many additional ones can be calculated by the use of Equations 1 and 2.

Polymerization of vinyl monomers requires that the monomers be present in a solution above certain minimal concentration. For acrylamide monomers, that minimal concentration is about 3% (w/v), or about 0.4M. Therefore, when the selected acidic and basic monomers are the sole monomers being polymerized, the sum of their concentrations will be at least about 3%. If desirable, it is possible to co-polymerize the charged monomers with another monomer having no charged groups. Examples of suitable monomers include acrylamide, N-vinylpyrrolidone, N,N-dimethylacrylamide, N-acryloyl-Tris(hydroxymethyl)aminomethane (NAT monomer, U.S. Pat. No. 5,319,046 to Kozulic et al.), N-Acryloyl-1-amino-1-deoxy-D-glucitol and other amino sugar monomers (U.S. Pat. No. 5,202,007 to Kozulic), and many others. This additional monomer may represent from 0.1 to 99.9%, on the molar basis, of all the monomers present in the polymerizing solution.

Many types of free-radical polymerization initiators can be used, including peroxides like benzoyl peroxide and lauryl peroxide, persulfates like ammonium persulfate and potassium persulfate, peroxydicarbonates like diisopropyl peroxydicarbonate, 2,2'-azobis(isobutyronitrile), 4,4'-azobis(4-cyanovaleric acid) and many others. Usually the initiators are present in the polymerization solution in amounts ranging from about 0.0002 to 0.2 percent by weight of the monomers. A catalyst, like N,N,N',N'-tetramethyletylenediamine (TEMED), may be added to control the rate of production of free radicals from persulfate initiators. Initiators for controlled, or living radical polymerization, may be employed as well.

Following polymerization, the resulting linear polymers will possess positively and negatively charged groups that define the isoelectric point of the polymer. Many such linear polymers of defined isoelectric points may be produced by selecting the charged monomers of various pK values in different ratios using Equations 1 and 2 or the already calculated and published formulations. If two polymerizing solutions are mixed to form a gradient, for example within a tube or a cassette, stabilized for example by a 30-0% glycerol gradient, then after polymerization a continuous series of linear polymers with slightly different pI values will be formed. Thus, this procedure may be used to produce polymeric carrier ampholytes, which may form smooth pH gradients and thus be advantageously used as a replacement for classic carrier ampholytes.

The linear polymers of defined isoelectric point prepared as described above need to become a part of a particle in order to make that particle isoelectric. When the linear polymer is of a high molecular mass (over about 1,000 kDa), the polymerization of other monomers in its presence to form a particle may result in physical entrapment of the isoelectric polymer. That physical entrapment may be sufficiently strong to prevent the polymer from leaving the particle in an electric field. Alternatively, the entrapped polymer may be cross-linked to the particle polymers, for example using a bis-epoxide (1,4-butanediol-diglycidylether), when the particle material contains hydroxyl groups. In a preferred alternative, the polymer is covalently linked to the particle. The link is established between a reactive group, or groups, of the linear polymer possessing a defined isoelectric point and a reactive group, or groups, of the particle. The reactive group on the polymer may reside on one of its ends, or the groups may reside on both of its ends, or along its length. Preferably, the group is on one of its ends. Such a group may be introduced in various ways, including the use of an appropriate chain transfer reagent or the RAFT polymerization, as disclosed for example in U.S. Pat. No. 6,642,318 to Chiefari et al. Both types of reactions are able to control the length of the polymer chains. A sulfhydryl group created after RAFT polymerization (Chiefari et al. Macromolecules 31:5559-5562, 1998) may be reacted, for example, with a maleimide or epoxy group of the particle to link the polymer to the particle and thus produce an isoelectric particle. This method of preparation of the isoelectric particles is a more preferred one.

The most preferred method of preparation of the isoelectric particles of present invention includes the formation of a three-dimensional network of polymers containing positive and negative charges and thus defining the isoelectric point of the particle. A three-dimensional polymer network is formed when a cross-linker, that is, a molecule containing more than one functional group, participates in the polymerization. This contrasts with the above described embodiment where the polymers may be cross-linked only after the polymerization. When it is desirable to form a three-dimensional network during polymerization, a cross-linker containing two or more vinyl double bonds is usually added to the polymerization solution. The cross-linker will contain no charged group in most cases, but a cross-linker with a charged group of a defined pK value may be employed as well. Illustrative cross-linkers comprise N,N'-methylene-bis-acrylamide, N,N'-ethylene-bis-acrylamide, ethylenglycoldimethacrylate and the cross-linkers described in U.S. Pat. Nos. 6,197,906 and 6,585,873 both to Solomon et al. The polymerizing mixture may contain additional monomers that carry no charge. Such monomers may contain functional groups that facilitate linking of a label to the particle or linking a member of a binding pair. For example, co-polymerization of acrolein will introduce aldehyde groups in the particle. A monomer having vicinal diol groups, like N-Acryloyl-1-amino-1-deoxy-D-glucitol or other amino sugar monomers (U.S. Pat. No. 5,202,007 to Kozulic), can be reacted with periodate to form aldehyde groups, or with 2,2,2-trifluoroethane sulfonylchloride to introduce a leaving group that is easily replaced in a reaction with a nucleophilic group of a binding member or of a label. There are many different variations of this procedure that may produce the desired particles. Several such variations, or embodiments, are described in detail below.

According to one preferred embodiment, an isoelectric particle of the present invention has a core-shell structure. The particles containing a single core-shell, or multiple shells, are known and some illustrative examples are disclosed in U.S. Pat. No. 5,091,206 to Wang et al., U.S. Pat. No. 6,136,891 to Chopin et al., U.S. Pat. No. 6,133,047 to Elaissari et al., U.S. Pat. No. 6,251,303 to Bawendi et al., U.S. Pat. No. 6,541,039 to Lesniak et al. and U.S. Pat. No. 6,548,264 to Tan et al. None of these references discloses a core-shell particle that contains polymers with the charged groups that define a pI value of the particle, as required for practicing the present invention. The core may be made of a material that is a label itself, or the core may contain a label. When, for example, the core is made of a colloidal gold particle (U.S. Pat. No. 6,214,560 to Yguerabide et al.), or of a nanocrystal (quantum dot, U.S. Pat. No. 6,251,303 to Bawendi et al.), or of a magnetic material (U.S. Pat. No. 5,091,206 to Wang et al., U.S. Pat. No. 6,013,531 to Wang et al., U.S. Pat. No. 6,133, 047 to Elaissari et al., and U.S. Pat. No. 6,541,039 to Lesniak et al.), then the core is the label. The mentioned core materials are all inorganic. The core may be made also of an inorganic and organic material, or of an organic material, for example polystyrene or polymethylmethacrylate, or of various copolymers. The particle may contain a label, such as a dye, or multiple dyes, fluorescent or non-fluorescent, adsorbed to the polymers as disclosed for example in U.S. Pat. No. 4,326,008 to Rembaum, U.S. Pat. No. 4,609,689 to Schwartz, U.S. Pat. No. 5,573,909 to Singer et al., U.S. Pat. No. 5,716,855 to Lerner et al, U.S. Pat. No. 5,786,219 to Zhang et al., and U.S. Pat. No. 6,514,295 to Chandler et al., or covalently linked to the polymers as disclosed for example in U.S. Pat. No. 5,897, 811 to Lesko and U.S. Pat. No. 5,286,803 to Lindsay et al. Particles may contain two labels, for example a quantum dot and a magnetic material, as described by Wang et al., Nano Letters 4:409-413, 2004. When any of the above described or similar particles constitute a part of an isoelectric particle of the present invention, additional polymers possessing the positively and negatively charged groups determine the isoelectric point of the particle. The isoelectric particles may be produced, for example, by polymerizing a solution of at least one positively charged monomer, at least one negatively charged monomer and a cross-linker, and optionally a neutral monomer, in the presence of a suspension of the selected particles containing a label or labels. Polymerization reactions in the presence of a particle are disclosed for example in U.S. Pat. No. 4,609,608 to Solc, U.S. Pat. No. 4,749,506 to Kitahara et al., U.S. Pat. No. 5,976,426 to Richard et al. and U.S. Pat. No. 6,274,387 to Yamauchi et al. The exact polymerization conditions will depend mainly on the size of the starting particles and on the desired sized of the isoelectric particles. A surfactant, or a particle stabilizing agent, may be added into the polymerization solution as disclosed in more detail herein below.

According to another preferred embodiment, the core is formed substantially simultaneously with formation of the polymers having charged groups. Thus, a fluorescent dye is dissolved in a hydrophobic monomer such as styrene or methylmethacrylate, which may contain a cross-linker such as divinylbenzene or ethyleneglycoldimethacrylate, respectively. A polymerization initiator, such as 2,2'-azobis(isobutyronitrile) is dissolved in the monomer-dye solution and added to a water solution containing a surfactant. Under stirring the hydrophobic monomer is dispersed in water forming small particles whose size is determined by the ratio of the monomer to the surfactant, as well as by the stirring speed. Suitable surfactants include, for example, SDS, Triton X-100, AOT, as well as polymerizable surfactants (reviewed by Summers et al., Advances in Colloid and Interface Science 100-102:137-152, 2003). The water solution will also contain at least one positively and at least one negatively charged monomer defining a desired pI value of the particles to be formed, and optionally an additional monomer and cross-linker. Free radicals generated by decomposition of the initiator, for example by raising the temperature to 60° C., under the atmosphere of an inert gas such as argon or nitrogen, will initiate polymerization of the hydrophobic monomer forming the core polymer, followed by, or simultaneously with, the polymerization of the charged monomers forming the shell. The pH of the polymerizing solution may be adjusted by an acid or a base, such as HCl or NaOH, in order to largely protonate, or deprotonate, the charged group of the monomer whose concentration is higher of the two charged monomers. In this way, the formed particles will acquire a net positive charge, or a net negative charge, thus reducing the tendency of the particles to aggregate.

According to yet another preferred embodiment, the polymers possessing charged groups that determine the isoelectric point of the particle form interpenetrating network within a suitable starting particle. Such starting particles comprise, for example, controlled pore glass particles, porous silica particles, porous polystyrene particles, porous polysaccharide particles and microgels formed of water soluble or water insoluble monomers. The particles may be composed of a single material, or they may be composed of several materials. For example, the particle may contain a silica shell covering a magnetic core, as for example disclosed in U.S. Pat. No. 6,548,264 to Tan et al. or described by Yang et al., Analytical Chemistry 76:1316-1321, 2004. When the particles contain silica, it is desirable that the silanol groups are either largely protected, by the reactions with dichlorodimethylsilane and methanol for example, or inaccessible to water, in order to reduce or eliminate the influence of silanol group charges on the pI of the particle. The polymer network formed by polymerization of the charged monomer and cross-linker molecules, and optionally other monomers, within pores of the particle may penetrate the whole interior of the particle, or only a part of its interior. The newly formed polymers may be grafted to the particle material by introducing polymerizable groups into the particles prior to the polymerization. For example, when the particle contains silica, then silanol groups are reacted with 3-trimethoxysilylpropyl methacrylate to introduce polymerizable double bonds. When the particle contains hydroxyl groups, they are reacted with allylglycidylether to introduce polymerizable vinyl groups. When the particle contains such polymerizable groups, it is possible to omit the cross-linker during the polymerization, so that the polymers having charged groups that determine the isoelectric point of the particle are grafted to the particle without being substantially cross-linked. The charged polymers may form also a shell around the starting particle, in addition to forming an interpenetrating network.

According to a further preferred embodiment, the isoelectric particle of present invention may consist substantially only of the cross-linked polymers bearing charged groups that determine the isoelectric point of the particle. Such particles may be prepared by polymerizing a solution containing at least one positively charged monomer, at least one negatively charged monomer, at least one cross-linker and optionally a neutral monomer, under the conditions that allow formation of the particles of defined size. Several methods exist for the production of polymeric particles of defined size. For example, particle preparation may take place by polymerization in reverse micelles (U.S. Pat. No. 4,521,317 to Candau et al. and U.S. Pat. No. 4,681,912 to Durand et al.), or in emulsions (Baade et al., European Polymer Journal 20:505-512, 1984), in a solvent in which the polymers are soluble (U.S. Pat. No. 5,354,481 to Neff et al., and U.S. Pat. No. 6,300,443 to Solomon et al.), or in a solvent in which the polymers are poorly soluble (U.S. Pat. No. 5,412,048 to Longley, and U.S. Pat. No. 5,635,574 to Aoyagi et al.). In the art, the particles may be known under various names, including colloid particles, colloids, latex, microspheres, microbeads, microparticles, microgels, nanoparticles, nanobeads and nanogels. Many practical and theoretical aspects of polymeric particles are addressed in a number of scientific publications, for example by Lowe et al., Polymer 39:1207-1212, 1998, Murray et al., Advances in Colloid and Interface Science 54:73-91, 1995, Kim et al., Polymer Journal 27:508-514, 1995, Saunders et al., Advances in Colloid and Interface Science 80:1-25, 1999, and Kawaguchi et al., Polymer Journal 23:955-962, 1991. In order to prevent particle aggregation, the particles are usually made to contain charged groups whose repulsion lowers the tendency of aggregation. Thus, the charge was negative when a monomer containing carboxylic group was used in the preparation of the particles, as disclosed for example in U.S. Pat. No. 4,560,714 to Gajria et al. Or, the charge was positive when an amino group containing polymer was used, as disclosed for example in U.S. Pat. No. 4,788,246 to Tsuchiya et al. Known are also zwitterionic polymers, containing both positive and negative charges in substantially equal number, as disclosed for example in U.S. Pat. No. 6,590,051 to Carter et al. Amphoteric polymers, containing an excess of quaternary ammonium groups over carboxylic groups, are disclosed in U.S. Pat. No. 5,380,444 to Ryan et al. Amphoteric polymeric microparticles are disclosed in U.S. Pat. No. 5,171,808 to Ryles et al. However, none of these charged polymers or particles is made with a selected ratio of positively and negatively charged groups of defined pK values that determine a predefined isoelectric point of the particle in the pH range of about 2.5 to 11. Thus, the polymers of Carter et al. and Ryan et al. do not have an isoelectric point in the 2.5-11 pH range. Ryles et al. teach that any combination of the mentioned anionic and cationic monomers could be used to produce the claimed amphoteric particles (column 2, lines 13-35), useful as flocculants in paper making. However, the majority of the monomer combinations of Ryles et al. would not produce an isoelectric particle of the present invention. For example, combining either 2-acrylamido-2-propanesulfonic acid or 2-acrylamido-2-methylpropanesulfonic acid (negatively charged monomers) with any of the mentioned positively charged monomers including acryloxyethyltrimethylammonium chloride, diallyldimethylammonium chloride, 3-(meth)acrylamidopropyltrimethylammonium chloride and methacryloxyethyltrimethylammonium chloride would not produce an isoelectric particle of the present invention because the pK values of both, the sulfonic acid group (pK around 1) and trimethylammonium group (pK above 12), lie outside the useful buffering range. Other monomers of Ryles et al. that contain a positively charged group are zwitterionic (3-acrylamido-propyltrimethylammonium-2-hydoxyproyl-methacrylate methosulfate and 1-trimethylammonium-2-hydroxypropyl-methacrylate methosulfate) with highly acidic pK (about 1) and highly basic pK (above 12), making them unsuitable for defining a pI value of an isoelectric particle of the present invention. The isoelectric particles of the present invention, having a predetermined isoelectric point in the pH range of about 2.5-11, and of about 5 nm to 100 µm in size may be formed by varying the parameters affecting the particle size, as disclosed and described in the above cited references. As a rule, reverse micelles are suitable for producing the particles having a size from a few nanometers to several hundred nanometers, while emulsions are suitable for producing the particles of several hundred nanometers to several hundred micrometers. The size of microgels produced without surfactants is usually from a few tenths of micrometer to a few tens of micrometers. The particles of defined sizes, but irregular shape, may be produced also by bulk polymerization followed by crushing and sieving the cross-linked polymer.

Large beads of defined pI values, prepared by emulsion polymerization of acrylamide, N,N-methylene-bisacrylamide and charged monomers, are known. Thus, Chiari et al. (Journal of Biochemical and Biophysical Methods 23:115-130, 1991) described beads of an average diameter of 200 µm and of isoelectric point of 6.2, useful for controlling the pH of tissue culture media. The use of even larger beads, 300-500 µm in diameter, for controlling the pH of a plant growth medium was described by Righetti et al. in Journal of Biotechnology 17:169-176, 1991. Further, Cretich et al. (Electrophoresis 24:577-581, 2003) described the use of beads of about 150 µm in diameter, and having various isoelectric points, for preparative isoelectric focusing, wherein the beads served the same role as the isoelectric gel membranes disclosed in U.S. Pat. No. 4,971,670 to Faupel et al. However, none of these prior art isoelectric particles is suitable for practicing a method of analyte detection, as disclosed in the present invention. The beads of Chiari et al., Righetti et al. and Cretich et al. are too large to be useful for capillary isoelectric focusing. Their particles would be unable to enter the capillaries currently in use for electrophoretic separations, because the diameter of these capillaries is from 50 to 200 µm. If their particles somehow entered a capillary of 200 µm in diameter, clogging of the capillary, rather than focusing at the isoelectric point, would be the most likely result. If somehow these large particles managed to focus at their isoelectric point, the number of particles that could occupy a typical focused zone of about 0.5 mm (Shen et al. Journal of Chromatgraphy, 914:257-264, 2001), would be only 2-3. Increasing the width of the focused zone 10 fold, also meaning decreasing the resolution 10 fold, would allow the focusing of 20-30 particles. Such a small number of particles is insufficient for any quantitative measurements of analytes. Finally, none of the above references suggests any possible use wherein the isoelectric particles would be made to migrate in a pH gradient under the influence of an electric field. On the contrary, Cretich et al. adopted various strategies to physically entrap the beads to prevent their migration in an electric field. The prior art isoelectric particles of 150-500 µm in diameter would be difficult or impossible to focus not only in the capillary format, but also in all other isoelectric focusing formats.

The isoelectric particles of the present invention will usually carry a label that allows for easy and sensitive detection of the particle. However, the particles without a label can be detected as well, for example by measuring light scattering (Xia et al. Langmuir 20:2094-2098, 2004). A label of the isoelectric particle of present invention may be exposed to the solvent employed during isoelectric focusing, or it may be inaccessible to that solvent. In most cases the solvent will be water, but other solvents, or mixtures of solvents can be used as well. When the label is a core of the particle made of gold or CdS, for example, then only the atoms or molecules on the core surface may be accessible to water. Also, when a dye is polymerized inside a droplet of a hydrophobic monomer, such as styrene, then the dye molecules will generally be inaccessible to water. On the other hand, when the label molecules are coupled to the particle after the particle has acquired its isoelectric point, the label molecules will generally be accessible to water. The same will be true if a vinyl derivative of a dye (U.S. Pat. No. 5,286,803 to Lindsay et al.) is copolymerized with the charged monomers determining the pI of the particle. When the label molecules are exposed to water and when they carry a charged group, the pI of the particle will be influenced by the label. While it is possible to make adjustments in the composition of the charged monomers to compensate for this influence of the label on the pI, or to take into account this contribution during the data analysis after isoelectric focusing, it is preferable that the label does not influence the pI of the particle. Therefore, the preferred labels are those that have no net charge in the pH range of about 2.5 to 11, and/or those labels that are inaccessible to water.

The label may consist of a cluster of atoms or molecules occupying a single position of the particle, for example its core. One may say that such a particle contains just one label entity. The label may comprise also multiple entities, for example a dispersion of many such clusters throughout the particle. Label entities may be present only in one shell of a multi-shell particle, or in multiple shells. Further, the label may consist of many molecules randomly bound to the material making the particle interior. Such label molecules may be present not only in the interior, but also on the particle surface. Or, they can be restricted only to the surface of the particle. In that case, the label molecules, or label clusters, should not interfere with the formation of specific binding pairs between the binding members. The label may be situated also between the particle and a binding member. However, the preferred location of the label is the interior of the particle.

A label in combination with a detector determines the sensitivity of an assay. The highest possible sensitivity, that is, the detection of the lowest possible amount of an analyte, is highly desirable when the analyte is present in a biological sample, because often only small amounts of sample are available and the analyte is usually present at a low concentration. With fluorescent labels, including fluorescent dyes and nanocrystals (quantum dots) which can be treated as fluorescent particles (Yguerabide et al., Analytical Biochemistry 262:157-176, 1998), it is possible to detect a single labeled particle (U.S. Pat. No. 5,573,909 to Singer et al. and U.S. Pat. No. 6,214,560 to Yguerabide et al.). A particle may contain from thousands to millions of fluorescent molecules (U.S. Pat. No. 5,607,864 to Ricchiero et al. and U.S. Pat. No. 5,716,855 to Lerner et al.). When such a particle is bound to an analyte through a binding member, the detection sensitivity may be three to six orders of magnitude higher compared to the sensitivity achievable when a binding member is labeled with a single label molecule. Moreover, the method of isoelectric focusing is capable of concentrating the analytes into narrow zones from a large starting volume, because initially the sample can occupy the whole volume of the separation tube or lane. Thus, this zone concentration factor in capillary isoelectric focusing is typically above 100 fold (Shen et al., Analytical Chemistry 72:2154-2159, 2000), and it can reach several thousand fold (Chen, et al. Journal of Proteome Research 2:249-254, 2003). The combination of the zone concentrating effect with the signal enhancement coming from the presence of many labels per particle of the present invention may lead to an improvement of sensitivity by five to nine orders of magnitude compared to the sensitivity achievable by solution-based assays. Capillary electrophoresis instruments equipped with laser detectors are commercially available (Applied Biosystems, Foster City, Calif.; Amersham, Beckman Coulter, Miami, Fla., and others). These instruments are designed mainly for DNA sequencing and therefore they are able to detect four different labels. When four groups of particles are prepared, each having one of the four suitable labels but all particles having identical pI value, then one zone formed during isoelectric focusing may contain information on four analytes. Such multiplexing increases the number of analytes detectable by the use of the isoelectric particles of present invention. It is expected that advances in laser-induced fluorescence detectors will further increase the multiplexing capability.

In contrast to the detectors that detect, and quantify, signals coming from specific labels on many particles in one zone, other detectors are capable of counting individual particles and quantifying signals coming from each single particle. The number of detected particles may be used as a measure of the amount of an analyte present in a sample. It is possible to positively identify the presence of a single analyte molecule in a sample when the detector is capable of detecting a single particle, if that particle formed a specific binding pair with the analyte. One such detector is a flow cytometer, commercially available from several companies (for example Partec, Münster, Germany, Becton Dickinson, Franklin Lakes, N.J., Beckman Coulter, Miami, Fla., and DakoCytomation, Glostrup, Denmark). In flow cytometry, particles in a liquid flow through a narrow tube illuminated with a suitable light that produces signals that can be correlated to one or several properties of each individual particle. Modem flow cytometers are capable of processing 50,000 particles per second. They are also capable of distinguishing multiple labels, commonly from 2 to 5, and up to 13 (Partec CyFlow ML multi-laser flow cytometer). When particles are made to contain several dyes in different proportions, a flow cytometer can distinguish the particles containing 64 such dye combinations (U.S. Pat. No. 6,514,295 to Chandler et al.). If the particles corresponding to each one of the 64 distinctive color groups are separately reacted to possess an isoelectric point according to the present invention, then each zone of a defined pI value formed during isoelectric focusing will be able to contain information on 64 analytes. Even a higher multiplexing capability is expected to result from further improvements in instrument design and/or label chemistry. Thus, at present 100 different color coded particles are available from Luminex, Austin, Tex. Therefore, the coupling of particle isoelectric focusing with a flow cytometer as the detector, as disclosed herein, brings significant advantages to the detection of multiple analytes. It is straightforward to calculate that a focused zone of 0.5 mm (Shen et al. Journal of Chromatography A 914:257-264, 2001) in a capillary of 200 µm diameter has a volume of $1.57 \cdot 10^7$ µm$^3$, and that this volume corresponds to the volume of $1.1 \cdot 10^6$ particles of 3 µm in diameter. If 50% of the volume of the focused zone is occupied by the particles, that would correspond to $5.6 \cdot 10^5$ particles. If these particles are labeled with 100 different dye combinations, to tag 100 analytes, there could be 5,600 particles of each dye combination. Such a number of particles is sufficient for a quantitative assay, covering a three orders of magnitude concentration range of each one of the 100 analytes. With a particle diameter of 0.3 µm, 5,600,000 particles of each one of the 100 dye combinations could be focused in a 0.5 mm wide zone.

While a combination of a label and a detector plays a key role in achieving the desired sensitivity and throughput, the choice of the binding members plays a key role in getting the desired specificity. One binding member of a specific binding pair will be linked to the isoelectric particle of present invention. A single particle will contain at least one molecule of the binding member. In practice, more than one molecule of the binding member will be linked to one isoelectric particle, and often hundreds or thousands of such molecules will be linked to one particle. It is preferred that the binding member is situated at the surface of the isoelectric particle. Members of the binding pair may be situated also in the interior of the particle, but due to the steric hindrance such members will have difficulties interacting with second members of the binding pair. In the ideal case, members of the binding pair will have no effect on the isoelectric point of the particle. However, this ideal case can be realized only when the members of binding pairs are all neutral molecules bearing no charge in the whole pH range covered by the isoelectric particles. Most biological molecules of interest do contain charged groups and therefore they will influence the isoelectric point of the particles. Their influence needs to be controlled, or eliminated, in order to achieve the needed focused zones by isoelectric focusing.

The elimination of the influence of the charged binding members on the pI value of the isoelectric particles may be realized by releasing the binding members from the particles prior to isoelectric focusing. This is straightforward when the binding members are linked to the particles through a reversible bond. For example, when the reversible bond is a disulfide, then the binding members are released by incubating the particles with an excess of a thiol reagent, such as dithiothreitol, for example. As the resulting thiol group itself is charged above about pH 8, it can be reacted with iodacetamide or N-ethylmaleimide to eliminate that charge. Another reversible bond is a vicinal diol cleavable by periodate. The resulting aldehyde is uncharged, but nevertheless it may be desirable to reduce it to an alcohol by sodium borohydride. Or, a light-(singlet oxygen) sensitive bond may be used, as described for e-tags (U.S. Pat. No. 6,686,152 to Singh et al.). Another possibility is to specifically degrade the binding member. Thus, when the binding member is a protein, treatment with a protease, like proteinase K, may remove all amino acids apart from those few through which the protein binding member was immobilized to the particle. In a similar fashion, a nuclease will degrade nucleic acid binding members. The approach wherein the label is released from a binding member prior to electrophoretic separation of the label is utilized in conjunction with electrophoretic tags (U.S. Pat. No. 6,686,152 to Singh et al.) and peptide based IEF tags (Cruickshank et al, Journal of Chromatography 817:41-47, 1998). Without releasing the binding member these prior art methods would not function, as the contribution of the binding member to the electrophoretic properties (charge and mass) or to the pI of the label would be overwhelming.

In contrast, the method of present invention may function also when the binding members are left linked to the particles during the isoelectric focusing step. The reason for this lies in the unique composition of the isoelectric particles of present invention. The isoelectric point of each particle is determined, depending on the particle size, by the ratio of hundreds, thousands, millions or even billions of charged groups of identical chemical structure. For example a particle of 5 nm in diameter would weigh $65.4 \cdot 10^{-21}$ g and contain about 260 charged monomer units, assuming that its density is 1 g/cm$^3$, that the average molecular weight of the charged monomers is 150 and that no other monomers are used during the polymerization apart from 1% of a cross-linker. An isoelectric particle of 5 µm in diameter would weigh $65.4 \cdot 10^{-12}$ g and contain 2.6 billion of charged monomer units, assuming that its density is 1 g/cm$^3$, that the average molecular weight of the charged monomers is 150 and that the charged monomers represent 1% of the weight of the particle. Contrary to that, the electrophoretic mobility of e-tags is determined by a charge/mass ratio of just one charged group, or a small number of charged groups, present in a small organic molecule (U.S. Pat. No. 6,686,152 to Singh et al.), or in a protein or short peptide (U.S. Pat. No. 5,824,478 to Müller and Cruickshank et al. Journal of Chromatography 817:41-47, 1998). When an isoelectric particle of the present invention possesses a thousand times larger number of the charged groups that determine its pI compared to the number of the charged groups contributed by a member of a binding pair, then the influence of these additional charges may be negligible. For example, it was found that between 20 and 150 femtograms ($10^{-15}$ g) of immunoglobulin G was immobilized to a particle of 5.6 µm diameter (U.S. Pat. No. 6,696,304 to Davies). A particle of that size has a volume of 91.9 µm$^3$. Assuming that the density of such a particle is 1 g/cm$^3$, then the particle weighs $9.19 \cdot 10^{-11}$ g. Thus, when $20 \cdot 10^{-15}$ g of IgG is immobilized to that particle, the weight ratio of the particle to the IgG is 4,595. When $150 \cdot 10^{-15}$ g of IgG is immobilized, the weight ratio is 613. Assuming that the charged groups represent about 2-3 times higher percentage in the weight of the particle compared to IgG molecules, the contribution of the protein charges to the total charges would be below 0.1%. This low amount may be negligible, at least for those isoelectric particles whose pI is close to the pI of the immobilized protein. Evidently, the lower the amount of the immobilized protein, the lesser is its influence on the pI of the isoelectric particle. The amount of $20 \cdot 10^{-15}$ g of IgG corresponds to about 80,000 IgG molecules immobilized on one particle. A smaller number of the first binding members immobilized on an isoelectric particle of the present invention may be sufficient for proper functioning of an assay. Therefore, the influence on the particle pI may be smaller than calculated above. The exact optimal number of molecules of the first member of a binding pair linked to the particle will depend primarily on the particle size, as well as on the affinity of the members of the binding pair and the stringency of the conditions used to separate the particles not participating in the formation of binding pairs.

When the influence of the charged groups of a binding member is non-negligible, then it can be controlled. One way of controlling it is as follows. Two sets of particles of identical pI but labeled with two different labels are prepared as described above. Then identical amounts of both particles are reacted with identical amounts of a binding member, such as a monoclonal antibody, under identical conditions. Both sets of particles will bind equal number of the monoclonal antibody molecules per particle, and therefore the pI of both particles will shift by the same value. Therefore, they will focus into one zone. Now, if the particles with the first label are allowed to interact with a specific antigen, for example from a tumor tissue, while the particles with the second label are allowed to interact with the same antigen from a normal tissue, it will be possible to measure the ratio of antigen concentrations in tumor and normal tissue, without releasing the antibody molecules prior to isoelectric focusing of the particles, by determining the ratio of signal intensity of the two labels focused in one zone. Instead of the ratio of signal intensity, a ratio of the number of the particles labeled with the first label to the number of the particles labeled with the second label can be determined using a flow cytometer. The same control strategy can be applied when a binding member is a nucleic acid. Peptide nucleic acids, which lack charged phosphate groups, may be advantageously employed to reduce the influence of the binding member on the pI of the particles. When a binding member is a monosaccharide, or a polysaccharide, its attachment to the isoelectric particle of present invention will not affect its pI. Labeled particles of a defined pI containing a first member of a binding pair may be isolated by preparative isoelectric focusing, if the above described methods yield only the particles of a broader pI distribution than desired.

The analyte bound through its binding member may remain attached to the particle during isoelectric focusing. However, it is preferred that the analyte is dissociated from the binding member prior to isoelectric focusing. The dissociation may be achieved by any method that does not affect a proper isoelectric focusing of the particle. For example, when the analyte is a protein and the binding member an antibody, the dissociation may be achieved by 8 M urea. Urea is fully compatible with isoelectric focusing. When nucleic acids are members of the binding pair, then urea, formamide or a high temperature may be employed. Degradation of a binding member, with a protease or nuclease as mentioned above, will also result in detachment or degradation of the analyte. It is also possible to dissociate the members of a binding pair by the use of a reagent that is incompatible with isoelectric focusing, for example 6M guanidinium chloride. Then, prior to isoelectric focusing, such a reagent will be removed from the isoelectric particles for example by centrifugation, filtration, gel filtration or magnetic separation.

The specific binding member will in most cases be covalently linked to the isoelectric particles of the present invention. However, other ways of a stable attachment exist. For example, in separate reactions avidin or streptavidin may be bound to the particles of a plurality of pI values. In other separate reactions, biotin may be linked to a plurality of different drugs, or drug candidates, or any molecules of interest in a library of compounds. Then, a specific drug-biotin conjugate is incubated with the particles of one defined pI containing avidin, forming a complex of the isoelectric particle-avidin-biotin-drug. When a plurality of such complexes is incubated with an immobilized protein suspected of interacting with a drug, those particles that carry the right drug will become immobilized, and thus specifically detectable. In this case, the specific binding member, the drug, is linked to the particle through a non-covalent bond, via the biotin-avidin binding pair characterized by an association constant of about $10^{15}$ $1^{-1}$ mol. Thus, two binding pairs, or more than two binding pairs, may be utilized in practicing the present invention. But in all cases a member of a specific binding pair will be immobilized to the isoelectric particle of the present invention. The release from an isoelectric particle of small molecular weight binding members may be unnecessary prior to the isoelectric focusing step.

Isoelectric focusing is a method of a high resolving power. When carrier ampholytes are employed, it is possible to resolve proteins that differ in their pI values by only 0.02 pH, whereas about ten times higher resolution, about 0.002 pH, is achievable by isoelectric focusing in immobilized pH gradients (*Immobilized pH Gradients: Theory and Methodology* by P. G. Righetti, Elsevier, Amsterdam, 1990, page 111). Regular immobilized pH gradient gels, typically containing about 4-5% (w/v) polyacrylamide, allow focusing of the molecules of a mass of up to about 500 kDa. Therefore, only the smallest isoelectric particles of the present invention may be focusable in such gels. Novel gel matrices of a higher porosity would be needed to allow focusing of the larger particles. Agarose gels are known to allow the migration of polystyrene particles of up to about 200 nm in diameter (Serwer et al. Analytical Biochemistry 158:72-78, 1986), but currently no agarose gels, or other highly porous materials, containing immobilized pH gradients are available. Not only polystyrene particles, but also cells and viruses have been separated by electrophoretic methods. Isoelectric focusing can be performed without ampholytes or immobilized pH gradients (U.S. Pat. No. 4,139,440 to Chrambach et al. and U.S. Pat. No. 5,447,612 to Bier et al.), or on the preparative scale (U.S. Pat. No. 6,638,408 to Speicher et al.), or using off-gel isoelectric focusing (Ros et al. Proteomics 2:151-156, 2002). While these methods may offer some advantages for focusing of the particles of the present invention, their resolving power is generally lower compared to the two most common methods of isoelectric focusing described above.

The resolving power achievable by the use of carrier ampholytes may be sufficient for many applications of the isoelectric particles of present invention. Assuming that the same resolution as with proteins, about 0.01 pH unit, will be achieved with the isoelectric particles of the present invention, 100 particles of different pI would be focused in one pH interval, or 700 particles of different pI values in the 3 to 10 pH interval. This assumption is in accordance with published results showing that capillary isoelectric focusing is capable of resolving 0.004 pI differences, resulting in the detection of 210 species in a complex protein extract (Shen et al., Analytical Chemistry 71:5348-5353, 1999). The expected maximal number of separable zones is about 720 (Shen et al., Analytical Chemistry 72:2154-2159, 2000). The exact number of the resolvable particle species of defined pI values will depend not only on the resolving power of the method of isoelectric focusing, but also on the accuracy and reproducibility of the production of the isoelectric particles of present invention. Inaccuracies in the concentrations of the charged monomers will influence the pI of the particles in dependence on how close the pI is to the pK value of the buffering charged monomer. Simulations show (*Immobilized pH Gradients: Theory and Methodology* by P. G. Righetti, Elsevier, Amsterdam, 1990, pages 96-98) that a 2% error will cause an error in the pI of between about 0.01 (when the pI is close to the pK on the pH side of protonated acids or deprotonated bases) and 0.1 pH unit (pI far from the pK on the pH side of deprotonated acids or protonated bases). Because of this effect, it may be desirable to produce the particles of unevenly spaced pI values, at shorter distances near the pK value of the buffering monomer and at larger distances away from the pK. If the achievable control of the monomer concentrations and other variables, for instance related to the polymerization process, dictated that the minimal practical pI difference between the isoelectric particles be 0.05 pH on the average, then 20 such particle zones would be resolvable per one pH unit, corresponding to 140 particles of different pI for the pH range of 3 to 10. Focusing in the pH range of 2 to 11 (possible but less common) would allow the separation of about 180 zones of isoelectric particles. In the former case, 140 different analytes could be detected in one isoelectric focusing run using a single label. As the common capillary electrophoresis detectors are able to detect four labels, 560 analytes may be detectable. If 100 dye combinations (Luminex) are used with the particles of a single pI value, then 14,000 different analytes may be detectable in one sample in one experiment by use of a flow cytometer as the detector. Or, 7,000 analytes may be detectable in two samples that are compared, or 4,677 analytes in three samples, etc, after just one isoelectric focusing run. This ability to simultaneously detect a large number of analytes using the method of the present invention compares favorably with other high capacity methods, such as two-dimensional gel electrophoresis and micro arrays. A major field of use of the method of present invention is the analysis of protein expression.

Capillary isoelectric focusing is a preferred format for separating and detecting the isoelectric particles of present invention. A fused silica capillary of 50-200 µm in diameter is commonly used for isoelectric focusing, but capillaries of smaller and larger diameters (from 2 to 700 µm), as well as square capillaries, are also available, for example from Polymicro Technologies, Phoenix, Ariz. One limitation of this format is the need to control the electroosmotic flow caused by charged groups on the inner wall of the capillary. The control is achievable in different ways, usually by coating the capillary wall with polymers (U.S. Pat. No. 4,680,201 to Hjerten, U.S. Pat. No. 5,069,766 to Zhu et al., U.S. Pat. No. 5,221,447 to Hjerten and U.S. Pat. No. 5,605,613 to Shieh) or small molecules (U.S. Pat. No. 4,931,328 to Swedberg). Another limitation is the need to mobilize the pH gradient when a detector is positioned at a fixed spot relative to the capillary. Any imperfections in the mobilization procedure will result in a loss of the resolving power. Successful procedures include chemical mobilization (U.S. Pat. No. 4,725,343 to Hjerten et al., and U.S. Pat. No. 5,110,434 to Zhu et al.), dynamic mobilization and pressure difference mobilization (Shimura, Electrophoresis 23:3847-3857, 2002). The ability to detect 210 protein zones, mentioned above, indicates that the existing mobilization procedures produce high quality results. While in most published references a detector was position at a fixed spot of the capillary, another instrument serving as a detector can be coupled to the capillary end. A mass spectrometer coupled to a capillary end represents a powerful system for the analysis of molecules in a complex sample, as reviewed by Shimura in Electrophoresis 23:3847-3857, 2002. A flow cytometer coupled to a capillary end will represent a novel powerful system for the analysis of multiple analytes using the isoelectric particles of present invention, as disclosed herein. Many difficulties associated with the coupling of mass spectrometry and capillary isoelectric focusing, discussed in the above mentioned reference, do not exist with flow cytometry because carrier ampholytes will not interfere with the detection of signals from the particles. Directing the flow of liquid carrying the isoelectric particles from the capillary end to a flow cytometer is straightforward, and can be achieved by the use of an electric field and chemical mobilization, or by hydrostatic mobilization, or by pumping. A sheath fluid may assist in carrying the isoelectric particles at a desired rate to pass by a light source of the flow cytometer. When the desired analysis time is about 60 min, of which 30 min is the effective particle detection time, at a detection rate of 50,000 particles per second 90,000,000 particles may be focused in a capillary. If 14,000 groups of different isoelectric particles (140 pI values, 100 colors) are used, each group may contain on the average 6,426 particles. This number of particles is sufficient for quantitative assay of all 14,000 analytes over a three orders of magnitude concentration range.

There exist other isoelectric focusing formats that may be preferable under certain circumstances. For example, micro-channel devices provide faster separations than capillary based systems, with the typical run times of 0.5-10 minutes versus 15-60 minutes (Hofmann et al., Analytical Chemistry 71:678-686, 1999), and they allow whole column detection (U.S. Pat. No. 5,468,359 to Pawliszyn). In place of a detector positioned at a fixed spot, a scanner may be used to detect the particles separated according to their pI. Thus, a long capillary can be scanned (Shimura, et al. Analytical Chemistry 74:1046-1053, 2002). A scanner, such as, for example, Odyssey produced by Licor (Lincoln, Nebr.) may be used to scan a gel. A gel may comprise a thermally reversible matrix, for example the one based on agarose or polyethyleneoxide-polypropyleneoxide (Yoshioka, et al. Analytical Biochemistry 323:218-223, 2003). With such a thermally reversible gel, the isoelectric focusing step may be carried out while the gel is in a semi-liquid or liquid state, to facilitate focusing of the particles, whereas the detection may be done while the gel is in a semi-solid or solid state. Other modifications of the experimental set up will be known to those skilled in the art.

The specification hereinabove contains details on the preparation of the isoelectric particles of present invention, on a label and a first binding member, as well as on the separation and detection of the isoelectric particles. In order to use the particles of the present invention in a method of analysis of a specific analyte, or analytes, it is essential that the first binding member interacts with a second binding member of the binding pair, where the second binding member is an analyte itself or an analyte derivative capable of a specific interaction and thus formation of a binding pair. The conditions optimal for establishing the interaction of the members of binding pairs, and for subsequent recovery of only those particles participating in the formation of binding pairs, will depend mostly on the nature of the binding pars. Thus, for example, in an embodiment where the analytes are cytokines, monoclonal antibodies against individual cytokines are attached to the isoelectric particles of different pI values. Monoclonal antibodies against cytokines are available, for example, from Sigma, St. Louis, Mo., and R&D Systems, Minneapolis, Minn. The attachment is carried out by formation of covalent bonds, for example between lysine amino groups of the antibodies and aldehyde groups of the particles. Any remaining aldehyde groups may be reduced with sodium borohydride, and any free monoclonal antibody molecules may be separated from the particles by gel filtration, ultrafiltration or centrifugation. A sample containing cytokines is treated in a standard way to extract all proteins. The essential subsequent step is immobilization of all proteins onto a solid surface. It is important that the immobilization step does not introduce a bias in the ratios of the proteins immobilized compared to the ratios of the proteins in the starting sample. Therefore, the proteins should be immobilized through a reactive group that is available on all proteins. Amino terminal and lysine amino groups are preferred. The solid surface may contain activated carboxyl groups, for example N-hydroxysuccinimide esters, or alternative reactive groups, for example epoxy, aldehyde or tosyl, or a combination thereof. After bringing the protein solution into contact with the activated solid phase under the conditions sufficient for coupling of proteins, followed by washing or another way of removing any unbound proteins and any byproducts, and optional inactivation of any remaining active groups on the surface, the immobilized proteins are brought into contact with a plurality of particles containing antibodies against selected cytokines. The amount of the particles is in excess relative to the proteins, that is, more than sufficient for complete saturation of the surface containing the immobilized proteins. Accordingly, some particles will not participate in the formation of a specific binding pair. When an antibody linked to a particle forms a specific binding pair with an immobilized cytokine, the particle itself becomes immobilized. After removal of the unbound particles, for example by washing the surface, only those particles that have formed a binding pair will remain bound to the solid phase. The number of particles of a defined pI-label combination, specific for one cytokine, correlates with the number of molecules of that cytokine immobilized onto the solid surface. Upon addition of 8M urea, or after digestion with proteinase K, for example, the particles are released from the solid phase, separated by isoelectric focusing and detected by a detector. The pI of each particle, or a combination of a label and pI, is correlated with an individual cytokine, whereas the intensity of the signal of each label is correlated to the amount of the cytokine. Or, the number of particles is correlated to the amount of the analyte.

Modifications of the above embodiment are possible. For example, all proteins in a sample may be reacted with N-hydroxysuccinimide ester of biotin (available from Pierce, Rockford, Ill., the same vendor sells also many cross-linking reagents that can be used to activate a solid surface). The biotinylated proteins are then attached to a solid surface via avidin (streptavidin) molecules that had previously been immobilized to the surface. In this way, the proteins present in the sample are attached to a surface through a non-covalent bond. Also a simple adsorption of proteins to a surface may provide adequate results in some instances. However, it is preferred to have proteins stably immobilized in order to use the conditions of adequate stringency for removing the isoelectric particles not participating in the formation of binding pairs. In another modification, a solid phase may contain a plurality of immobilized antibodies specific for the analytes of interest. Thus, after washing away other species only the analytes of interest would remain bound to the solid support. This sandwich-type format may increase the specificity of the assay. In yet another modification, a group specific binding member may be immobilized to a solid phase. Examples of such a group specific binding member include protein A, protein G and a secondary antibody, which are capable of forming specific binding pairs with immunoglobulin molecules that recognize various antigens. Other antibodies against the same antigens would then be the specific binding members linked to the isoelectric particles of the present invention. When the antigens are allergens, the method may be suitable for detecting the presence and amount of the antibodies against the selected allergens.

The solid phase may be a well of a microtiter plate, an inner surface of a tube, a column filled with particles, a filter containing fibers or particles, a monolith column, a plurality of particles dispersed in a solution, or any other material that allows direct or indirect immobilization of analytes, adequate access of the isoelectric particles to the immobilized analytes and adequate separation of those isoelectric particles which formed a binding pair from those particles which did not form a binding pair. The preferred procedure for separating the bound from unbound particles depends mostly on the nature of the solid phase, and may comprise washing, filtration, centrifugation, sedimentation or magnetic separation. A preferred solid surface is the surface of magnetic particles. Magnetic particles with reactive groups on their surface, where the reactive groups comprise carboxylic acid, tosyl, aldehyde or hydrazide, are commercially available, for example from Dynal Biotech, Oslo, Norway, Polysciences, Warrington, Pa., and Seradyn, Indianapolis, Ind. Immobilization of the analytes, that is, of the second binding members of the binding pairs, may be carried out under the conditions recommended by the manufacturer or under modified conditions selected by a person skilled in the art. When using magnetic particles for immobilizing the second members of the binding pairs, it is preferable that the size of the magnetic particles is larger than the size of the isoelectric particles carrying first members of the binding pairs, at least by a factor of about 2, preferably by a factor larger than 3. If the isoelectric particles of the present invention contain a magnetic material, the use of a magnetic field may facilitate separation of the free from solid phase bound particles, in a way described by Luxton et al. Analytical Chemistry 76:1715-1719, 2004.

All second binding member molecules immobilized on a solid phase may not be able to form a binding pair. The method of the present invention does not require that all immobilized binding members form a binding pair, or that all binding members on the isoelectric particle form a binding pair. However, it is desirable that as many as possible binding pairs are formed with the second binding members (analytes) immobilized on a solid phase because this increases the sensitivity and accuracy of the method. Steric hindrance is a major reason why some molecules immobilized on the solid phase will be unable to form a binding pair. An isoelectric particle that has formed a binding pair will hinder the formation of additional binding pairs between other particles and all immobilized molecules that happen to be in its vicinity, where the vicinity corresponds approximately to the diameter of the particle. Evidently, small particles cause less steric hindrance. When a certain particle size is desired, for example for proper detection using a specific detector, the extent of steric hindrance can be controlled in several other ways. For example, taking a large ratio of the activated surface compared to the amount of the analyte molecules to be immobilized on that surface will result in spreading of the immobilized molecules more apart than when a low ratio is employed. Further, if an inert carrier, not able to form a specific binding pair but able to compete for the active groups on the surface, is mixed with the analyte molecules prior to their contact with the activated surface, the analyte molecules will be separated by the areas occupied by the inert carrier. The inert carrier may be a protein, bovine serum albumin for example, a polymer containing amino group, or groups, when proteins are immobilized through lysine groups, a small molecular weight compound, or the like, depending on the exact nature of the analyte and the immobilization chemistry. When a sample contains a large amount of one analyte whose detection is of no interest, for example albumin in human serum, then that analyte can serve as a natural carrier. Thus, the method of present invention is well suited for the analysis of such samples, in contrast to other methods, like two-dimensional gel electrophoresis, where the presence of one analyte at a high concentration represents a major problem.

In the preferred embodiments of the method of the present invention the formation of specific binding pairs takes place while the second members of binding pairs are immobilized on a solid phase. The formation of specific binding pairs may take place also in solution, between the first members of the binding pairs linked to the isoelectric particles and the second members of the binding pairs dissolved in a solution. However, this is a less preferred embodiment because it may lead to a reduced sensitivity of the assay. In another embodiment, a competitive assay format may be employed. In this format, the signal detected is inversely proportional to the quantity of the analyte. Thus, for example, the isoelectric particles of the present invention may contain an analyte or analyte analogue as a first member of a binding pair. A second member of the binding pair may be immobilized on a solid surface. When a sample contains no analyte, the isoelectric particles will bind to the solid surface. When the sample contains the analyte, that analyte will compete with the analyte immobilized on the isoelectric particles, and therefore fewer isoelectric particles will bind to the solid surface. Instead of measuring the isoelectric particles bound to a solid phase, one can measure those particles that have remained free. In such an assay format, it is important to know the precise number, or concentration, of the starting particles. A solution containing a selected number of particles may by prepared, for example, by a cell sorter. Other assay formats will be known to those skilled in the art.

The detection and quantification of analytes in accordance with the method of the present invention is advantageous also in that multiple internal and external controls are possible. Thus, if several particles of identical pI all contain an identical member of a specific binding pair but different labels, the results of analysis should be identical with all particles. Any differences would be directly related to the inherent variability of the method. Further, when comparing analytes from two or more samples, the particles that formed specific binding pairs in all samples may be combined prior to isoelectric focusing. That would eliminate any bias due to the variables associated with the focusing and detection steps. In addition, external pI markers, that do not have to be the isoelectric particles of present invention, can be used to provide a control for proper functioning of the separation and detection steps. For example, fluorescent pI markers (U.S. Pat. No. 5,866,683 to Shimura et al.) may provide a precise control of the successful creation and maintenance of the pH gradient. In yet another control aspect, the solid phase containing covalently immobilized analytes may be reused if the dissociation of the binding pairs is carried out under the conditions that do not destroy the analytes. For example, denaturation of proteins by urea is reversible. Performing a second assay with the same immobilized analytes would provide information on the reproducibility of the method. The immobilized analytes may be stored for future re-checking, if the need arises. For constructing a standard curve necessary for the quantification of analytes, usually 5-10 different analyte concentrations are used. Hundreds of analytes, each of a known concentration, may be mixed together prior to incubation with the labeled isoelectric particles carrying specific binding members, and then all the particles that have participated in the formation of binding pairs at all different concentrations of the analytes may be combined prior to the isoelectric focusing step. In this way, any variations occurring during the separation and detection steps will affect all analytes at all concentrations in the same way, improving accuracy of the method. Due to the high multiplexing power of the method of present invention, the particles participating in the formation of specific binding pairs in a sample may be combined with those particles used for constructing the standard curves, followed by isoelectric focusing, detection and quantification, thus further increasing the accuracy. Finally, each isoelectric particle-label-first member of the binding pair can be manufactured in a large batch and then subjected to quality control. Therefore, thousands, or millions, of assays may be performed with such particles of a single batch. This capability of batch production and quality control makes the method of the present invention advantageous in comparison with microarrays.

The labeled isoelectric particles of present invention represent useful coding compositions also when they carry no member of a specific binding pair. For example, the particles of one defined pI value and carrying a label may be added to a material whose traceability is desired. Tagging of materials can be performed in different ways and for different purposes, as disclosed for example in U.S. Pat. No. 5,641,634 to Mandecki, U.S. Pat. No. 6,372,428 to Nova et al., and U.S. Pat. No. 6,465,193 to Akeson et al. The isoelectric particles of the present invention may be employed as tags for food, drugs or other products in order to allow tracing of the production batches or for counterfeit control. If combinations of two or more unique particles of defined pI and label are used as a coding composition, the number of the combinations is huge when starting with a set of 14,000 different particles (140 pI values, 100 dyes).

Kits may be prepared that contain a plurality of the isoelectric particles of present invention. If the particles are not labeled, they will contain functional groups that allow labeling, and the kit will comprise suitable labels and other reagents needed for the labeling. In a kit comprising a plurality of labeled isoelectric particles, the particles may contain functional groups that allow coupling of the first members of binding pairs, or of a ligand through which the first binding members is linked to the particles. The kit may comprise also members of the first binding pair. Another kit may comprise a plurality of the isoelectric particles of present invention, containing a label and a first member of the binding pair both linked to the particles. The kit may contain also analyte controls. A kit may comprise additional materials necessary for practicing the method of the present invention, for example carrier ampholytes, pI markers and/or a gel for isoelectric focusing. A further kit may comprise also software that is helpful for data acquisition and/or analysis.

All cited references are incorporated expressly hereinabove by way of reference in their entirety.

The principles, preferred embodiments and modes of operation of the present invention have been described in the foregoing specification. The invention, which is intended to be protected herein, however, is not to be construed as limited to the particular forms disclosed, since these are to be regarded as illustrative rather than restrictive. Variations and changes may be made by those skilled in the art without departing from the spirit of the invention as defined by the appended claims.

What is claimed is:

1. A plurality of particles of a size of about 5 nm to 50 μm and having a predetermined isoelectric point in a pH range of about 2.5 to 11, each particle comprising at least 100 positively and negatively charged groups respectively derived from at least one organic acid monomer and at least one organic base monomer, wherein the ratio of said monomers is selected such that after free radical copolymerization their charged groups determine the isoelectric point of the particles, wherein, under the influence of an electric field, the particles are adapted to migrate in a medium containing a pH gradient formed by carrier ampholytes and to focus at a position in the pH gradient that is not broader than 0.2 pH units and corresponds to their isoelectric point.

2. A plurality of particles of claim 1, wherein the positively and negatively charged groups are selected from the group consisting of carboxylic, sulfonic, phosphonic, amino, trialkylammonium and guanidino groups.

3. A plurality of particles of claim 1, wherein the pH gradient with carrier ampholytes is created in a capillary having a diameter of about 50 to 200 μm.

4. A plurality of particles of claim 1, further comprising a label.

5. A plurality of particles of claim 4, wherein the label comprises an inorganic material.

6. A plurality of particles of claim 5, wherein the inorganic material is selected from the group consisting of colloidal gold, nanocrystals, magnetic material, glass and silica.

7. A plurality of particles of claim 4, wherein the label comprises an organic material.

8. A plurality of particles of claim 7, wherein the organic material is a fluorescent dye or a non-fluorescent dye.

9. A plurality of particles of claim 1, further comprising a first member of a binding pair linked to the particles, wherein the presence of said first member of the binding pair has a negligible effect on the pI of the particles.

10. A plurality of particles of claim 1, further comprising a label.

11. A plurality of particles of claim 10, wherein the first member of a binding pair is selected from the group consisting of a protein, a synthetic nucleic acid, a natural nucleic acid, a monosaccharide, a polysaccharide and biotin.

12. A plurality of particles of claim 1 wherein the monomers comprise acrylamido groups.

13. A kit comprising at least two groups of particles, each group of particles comprising a different plurality of particles as claimed in claim 1.

* * * * *